United States Patent [19]
Heinix

[11] Patent Number: 4,611,991
[45] Date of Patent: Sep. 16, 1986

[54] APPARATUS FOR FIXING A PLASTER CAST IN AN ARTICULATOR FOR THE PRODUCTION OF DENTAL PROSTHESES

[75] Inventor: Lucien J. C. Heinix, Antwerp, Belgium

[73] Assignee: Alphadent, Belgium

[21] Appl. No.: 743,830

[22] Filed: Jun. 12, 1985

[30] Foreign Application Priority Data

Sep. 3, 1984 [BE] Belgium ............................... 2/60489

[51] Int. Cl.$^4$ ............................................. A61C 11/00
[52] U.S. Cl. ......................................... 433/60; 433/54; 433/73
[58] Field of Search ....................... 433/54, 60, 72, 73, 433/55, 56, 57, 58, 59, 61, 62, 63, 64, 65, 66, 67, 68, 69

[56] References Cited

U.S. PATENT DOCUMENTS

| | | | |
|---|---|---|---|
| 1,050,933 | 1/1913 | Evans | 433/73 |
| 2,040,835 | 5/1936 | Cubbage | 433/72 |
| 3,052,030 | 9/1962 | Spence | 433/73 |

Primary Examiner—John J. Wilson
Attorney, Agent, or Firm—Bacon & Thomas

[57] ABSTRACT

Apparatus for fixing a plaster cast in an articulator for producing dental prostheses, including a three-point support (5) which is mainly defined by a body (8) to which two coaxial projections (15,16) are fixed and with which a small lath (11) is slidably received, the longitudinal direction of the lath (11) being perpendicular to the general longitudinal direction of the projections (15,16).

9 Claims, 9 Drawing Figures

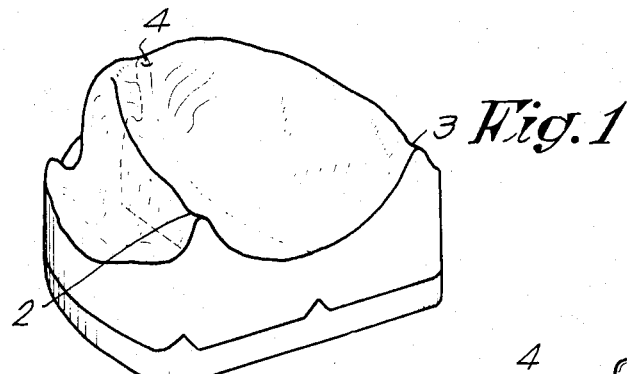
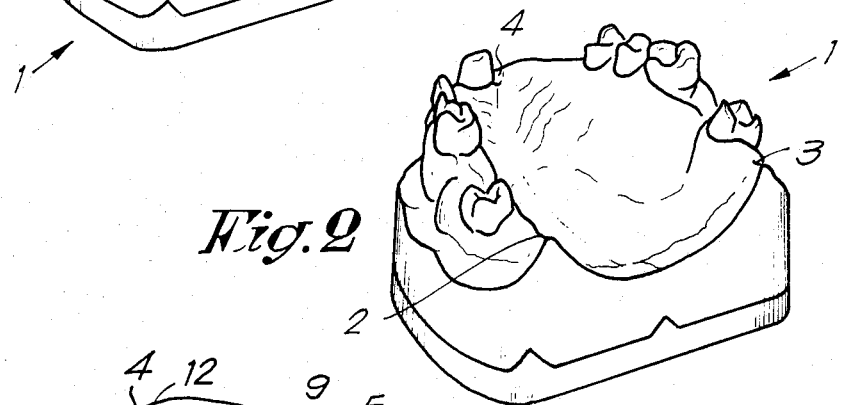
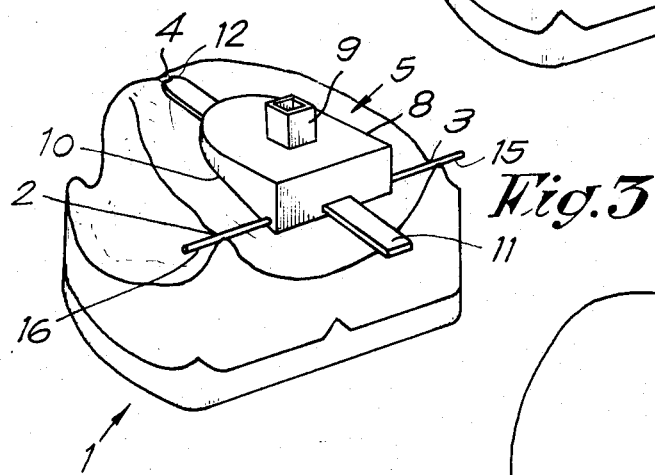
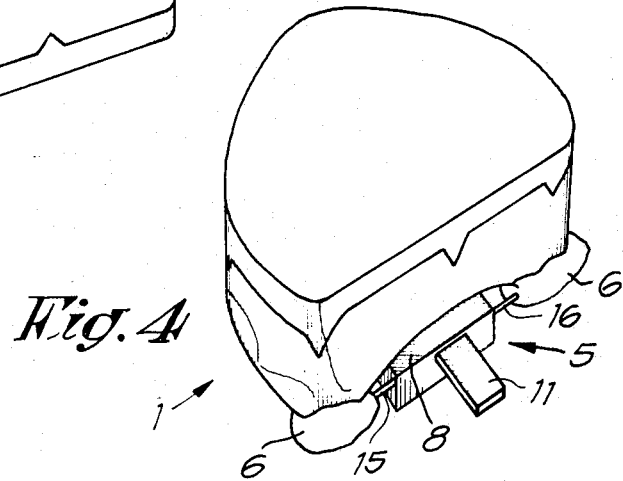

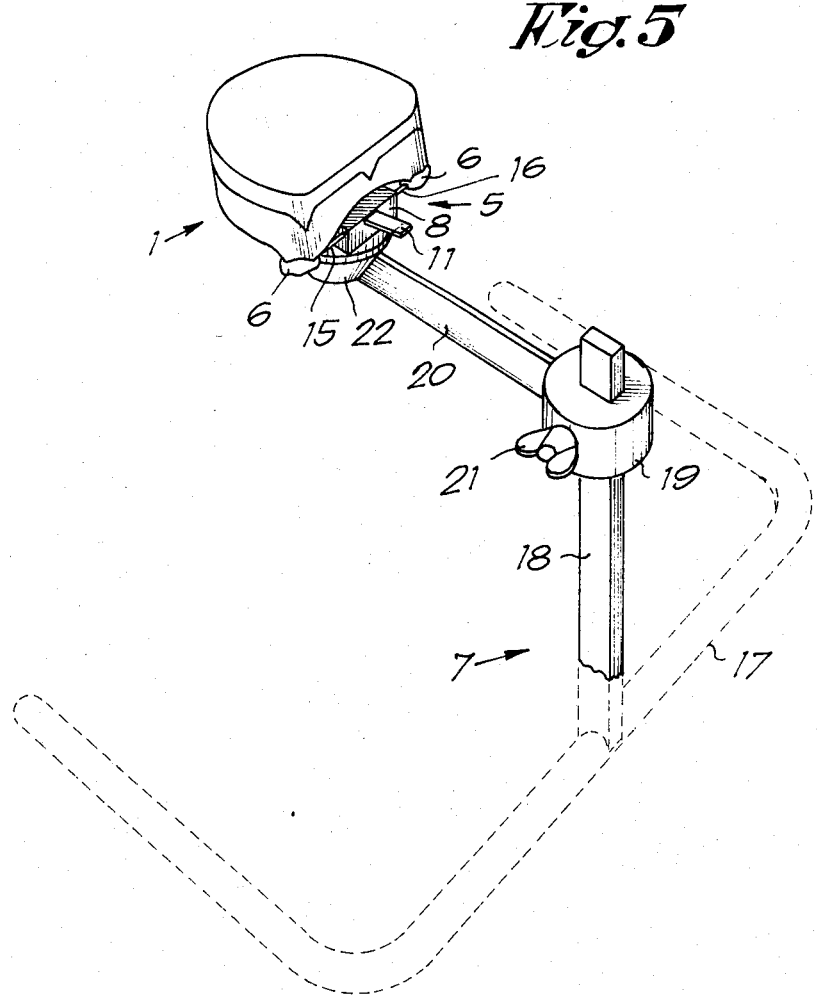

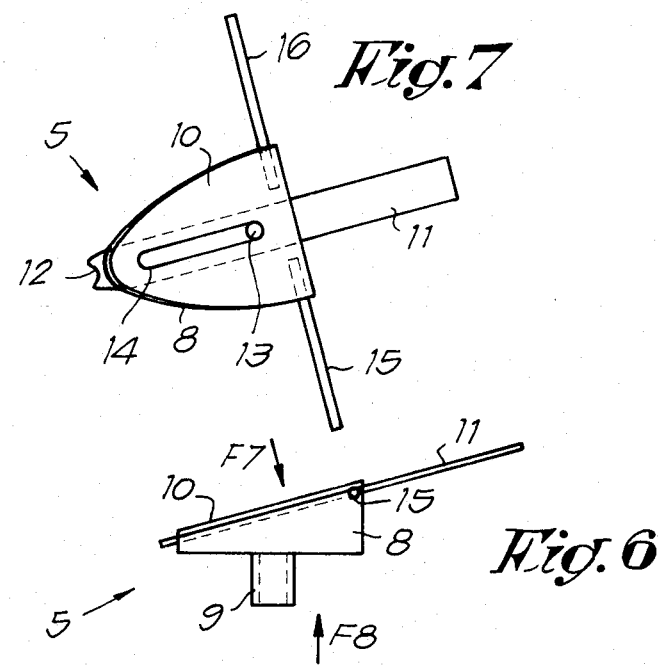
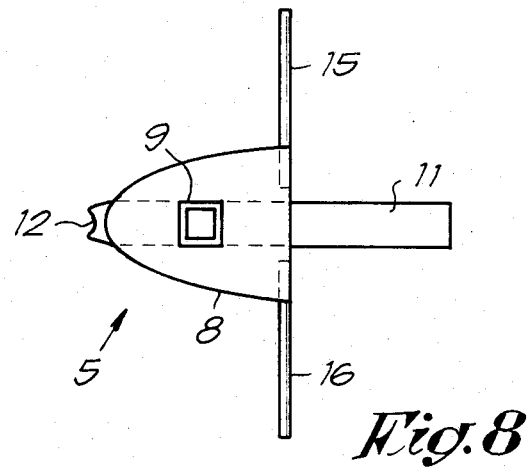

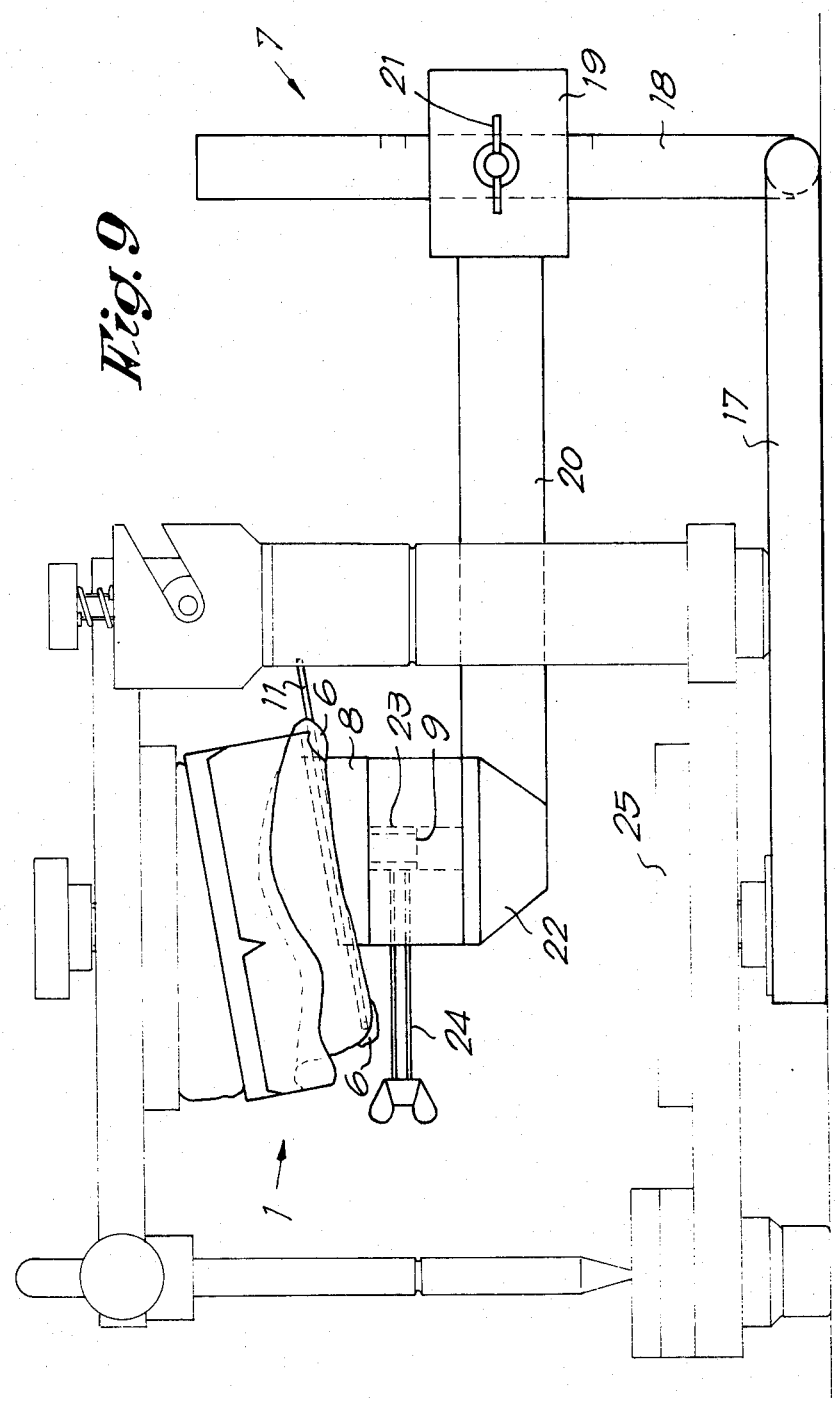

APPARATUS FOR FIXING A PLASTER CAST IN AN ARTICULATOR FOR THE PRODUCTION OF DENTAL PROSTHESES

BACKGROUND OF THE INVENTION

The present invention relates to an apparatus for fixing a plaster cast in an articulator for the production of dental prostheses.

More especially, the present invention relates to an apparatus for correctly fixing plaster casts in an articulator if no individual anatomic information about the patient, such as e.g. the so-called facial arc, is available.

SUMMARY OF THE INVENTION

For that purpose, the main object of the invention is that the plane formed by the three anatomical points of the upper plaster cast is placed into the articulator parallel to the so-called plane of Camper.

The three points are formed by both the pterygomaxillary folds and the papilla incisiva.

This apparatus consists of a three-point support by means of which the upper plaster cast can be fixed in the abovesaid three points.

It is clear that the apparatus is not articulator-bound.

BRIEF DESCRIPTION OF THE DRAWINGS

In order to better indicate the characteristic features of the invention, a preferred embodiment will be described below as an example without limiting the scope of the present invention with reference to the accompanying drawings wherein:

FIG. 1 is a perspective view of a toothless plaster cast.

FIG. 2 is a view analogous to that of FIG. 1, but for a partly toothed plaster cast.

FIGS. 3 and 4 are perspective views of the relative arrangement and the fixation of a three-point support according to the invention on a plaster cast.

FIG. 5 is a perspective view of a standard to which the plaster cast according to FIG. 4 has been applied.

FIG. 6 is a side-view of the three-point support as applied in the FIGS. 3 and 4.

FIGS. 7 and 8 are views according to the direction of arrows F7 and F8 in FIG. 6.

FIG. 9 is a side-view of an articulator wherein a plaster cast according to the invention has been fixed.

According to the present invention, an upper plaster cast 1 may be first ground all around, whereupon the three anatomical points of the upper plaster cast are indicated, viz. both pterygomaxillary folds 2-3 and the papilla incisiva 4.

Thereupon, an upper plaster cast, supported in both pterygomaxillary folds 2-3 and the papilla incisiva 4 on the one hand, with these three anatomical points in a plane parallel to the so-called plane of Camper at the required height with respect to the incisal height indicated by the manufacturer of the articulator, is suitably fixed with the upper arm of the articulator, as is schematically represented in FIG. 9.

Thereafter, the lower cast can be fixed at the right place to the articulator basis by means of the so-called biterims.

According to the present invention, one will preferably apply a three-point support 5 to the anatomical points 2, 3 and 4, after having indicated the latter points on the plaster cast, whereupon the plaster cast 1 and the three-point support 5 are joined with each other by means of an adhesive wax 6 in the abovesaid three points 2, 3 and 4 whereafter the whole is placed on a standard 7, which allows the plaster cast 1 to be brought in the right position in the articulator.

In order to avoid any mutual rotation of the three-point support 5 with a support or the like 7, the projection 9 has the configuration of a non-round section, in this case a square section.

In the longitudinal direction of the three-point support 5 a small lath 11 is provided parallel to the top face 10 of the body 8, which lath 11 is freely slidable in the latter body 8 and preferably has a recess 12, that allows the lath 11 to be suitably placed against the papilla incisiva 4.

Preferably, lath 11 in addition is provided with a projection 13 which co-operates with a slot 14 in body 8 in order to prevent such lath 11 from being lost.

Finally, the three-point support 5 is completed by rod-like projections 15-16 perpendicular to lath 11, the projections being made of two parts that are fixed in body 8 and having the purpose of supporting the pterygomaxillary folds of the plaster cast on the ends of these projections.

The plane containing the small lath 11 and the projections 15-16 preferably forms an angle of about 9°30' with respect to the base of body 8.

FIG. 5 schematically represents a standard 7 with which the three-point support 5 can co-operate, the standard in this case being made of a U-shaped base 17, both elements being such that the standard can be easily placed between and/or around the small legs of an articulator. To this base 17 a vertical support or column 18 is fixed, and the end 19 of an arm 20 is slidably supported over the latter the end, wherein a pressure means 21 is provided for securing the arm 20 at a suitable height.

The second end 22 of arm 20 is provided with a bore 23 directed perpendicularly to the base 17, the projection 9 of the three-point support 5 accurately fitting this bore, and a pressure means 24 being provided in the end 22 allowing end 9 of support 5 to be fixed in arm 20.

Marks can be provided on column 18 of standard 7 for indicating the approximative height of arm 20 for various types of articulators so that the height of arm 20 can be simply determined.

After the upper cast has thus been fixed correctly, the lower cast is fixed by means of plaster to the basis 25 of the articulator, use being made of the so-called bite-rims for positioning.

Although in the description reference is always being made to a three-point support, it is evident that a doubling of the free end of the lath 11, with the purpose of acting on both sides of the papilla incisive 4, likewise falls within the scope of the invention. It is clear that the present invention is by no means limited to the above-described embodiment and that such apparatus can be made in whatever shapes and dimensions without departing from the scope of the invention.

I claim:

1. An apparatus for fixing a plaster cast in an articulator for the production of a dental prosthesis defining a plane encompassing the pterygomaxillary folds and the papilla incisiva, which apparatus comprises:
   (a) a three-point support for engaging the pterygomaxillary folds and the papilla incisiva;
   (b) the support including a body;

(c) two coaxial elongate projections secured to the body for engaging the pterygomaxillary folds;

(d) an elongate lath carried by the body and slidably movable with respect thereto for engaging the papilla incisiva; and (e) wherein the longitudinal axes of the projections are disposed perpendicular to the longitudinal axis of the lath.

2. The apparatus of claim 1 wherein the lath is disposed at an angle with respect to the base of the body.

3. The apparatus of claim 2 wherein the angle is approximately 9°30′.

4. The apparatus of claim 2 and 3 wherein the body is of a triangular configuration when viewed from the side thereof, the lath being secured in a parallel disposition to the bolique upper face of the body, and the projections are secured at the highest point of the body.

5. The apparatus of claim 3 wherein the projections and the lath are disposed in a common plane.

6. The apparatus of claim 1 wherein the lath includes a free end provided with a recess therein.

7. The apparatus of claim 1 wherein the body includes a projection extending from the base thereof and disposed perpendicular thereto.

8. The apparatus of claim 7 wherein the projection is of a rectangular configuration.

9. The apparatus of claim 1 wherein the body includes a base disposed in a horizontal plane and both the lath and the projections are disposed in a plane parallel to the plane of Camper.

* * * * *